United States Patent
Choudary et al.

(10) Patent No.: US 6,906,216 B2
(45) Date of Patent: Jun. 14, 2005

(54) PROCESS FOR THE SYNTHESIS OF N-SUBSTITUTED β-AMINO NITRILES THROUGH THE RING OPENING OF AZIRIDINES

(75) Inventors: Boyapati Manoranjan Choudary, Andhra Pradeah (IN); Jeyalakshmi Kulandaivelu, Andhra Pradeah (IN); Pravin R. Likhar, Andhra Pradeah (IN); Lakshmi Kantam Mannepalli, Andhra Pradeah (IN); Sreedhar Bojja, Andhra-Pradeah (IN); Bhanuprakash Kotamarthi, Andhra-Pradeah (IN); Sitha Sanyasi, Andhra-Pradeah (IN)

(73) Assignee: Council of Scientific and Industrial Research, New Delhi (IN)

( * ) Notice: Subject to any disclaimer, the term of this patent is extended or adjusted under 35 U.S.C. 154(b) by 105 days.

(21) Appl. No.: 10/306,745

(22) Filed: Nov. 29, 2002

(65) Prior Publication Data

US 2004/0198999 A1 Oct. 7, 2004

(51) Int. Cl.$^7$ .................... C07C 253/00; C07C 255/00
(52) U.S. Cl. .................... 558/309; 558/431; 558/452
(58) Field of Search ................... 558/309, 431, 558/452

(56) References Cited

PUBLICATIONS

Farras et al., "beta–Amino Acids by Nucleophilic Ring–Opening of N–nosyl Aziridines", Tetrahedron, Elsevier Science Publishers, Amsterdam, NL, vol. 57, No. 36, Sep. 3, 2001, pp. 7665–7674, XP004302830.

Yadav et al., "First Examples of C–arylation of Aziridines Catalzed by Indium Triflate", Tetrahedron Letters, Elsevier Science Publishers, Amsterdam, NL, vol. 42, No. 45, Nov. 5, 2001, pp. 8067–8070, XP004309986.

Matthews et al., "Synthesis of Novel Sila–Substituted Beta–Amino Acids", Tetrahedron Letters, Elsevier Science Publishers, Amsterdam, NL, vol. 43, No. 31, Jul. 29, 2002, pp. 5401–5404, XP004371605.

Matsubara et al., "Yb(CN)3–Catalyzed Reaction of Aziridines with Cyanotrimethylsilane", Tetrahedron Letters, vol. 31, No. 44, 1990, pp. 6379–6380, XP002250042.

*Primary Examiner*—Johann Richter
*Assistant Examiner*—Ebenezer Sackey
(74) *Attorney, Agent, or Firm*—Nixon & Vanderhye P.C.

(57) ABSTRACT

The present invention comprises the simultaneous ring opening and concomitant N-substitution of various N-tosyl aziridines with different aliphatic and aromatic nitriles in presence of catalytic amount of metal triflates to afford different N-substituted β-amino nitriles in excellent yields and selectivities.

9 Claims, No Drawings

PROCESS FOR THE SYNTHESIS OF N-SUBSTITUTED β-AMINO NITRILES THROUGH THE RING OPENING OF AZIRIDINES

FIELD OF THE INVENTION

The present invention relates to a process for the synthesis of N-substituted β-amino nitriles, precursors to β-amino acids by the simultaneous ring opening of aziridine and concomitant alkylation, using aliphatic and aromatic nitrites. The unique activation of organo nitrile is catalyzed by metal triflates to facilitate simultaneous ring opening and N-alkylation of activated aziridines to give N-substituted β-amino nitriles, precursors to β-Amino acids in excellent yields in a single pot for the first time.

BACKGROUND OF THE INVENTION

β-Amino acids are widely used intermediates for the synthesis of biologically active compounds such as β-lactams and β-peptides. N-substitution of β-peptides exhibits increased potency and selectivity because of enhanced hydrophobicity, improved bioavailability and metabolic stability. Ring op of aziridines, which is an important and widely used protocol due to ease of preparation, ring strain and high reactivity, is increasingly appreciated because of their application as versatile building blocks for the synthesis of many nitrogen containing biologically interesting molecules.

Although β-amino nitrites are conveniently prepared by the ring opening of aziridines with trimethylsilyl cyanide, bromoacetonitrile, alkali cyanide, the unsatisfactory selectivity, low yield and use of hygroscopic/hazardous chemicals make these methodologies less attractive. Moreover, post alkylation of β-amino nitriles/acids and related peptide is very difficult endeavor.

Synthesis of β-amino nitriles by the nucleophilic ring opening of N-nosyl aziridines with cyanide ions followed by hydrolysis of corresponding nitrites to give N-nosyl β-amino acids is disclosed in *Tetrahedron* 2001, 57, 7665. The inherent disadvantages are the use of toxic reagents and cumbersome methodology. Synthesis of β-amino nitriles from aldimines and bromoacetonitrile in presence of tin powder and trimethylsilyl chloride is disclosed in *Synth. Comm.* 1997, 27, 3175. The inherent disadvantage is the usage of expensive reagents.

The ring opening reaction of aziridine with trimethylsilyl compound triggered by tetrabutylammonium fluoride to give corresponding products regioselectively is disclosed in *J. Org. Chem.* 2000, 65, 1344. This disclosure provides the protocol for the ring opening reaction of aziridine to afford cyano, azido, or chloroamines. However, the inherent disadvantages of this procedure are the use of hygroscopic silyl compound, unsatisfactory selectivity and moderate yield in some cases.

The reaction of Schiff bases such as N-benzylideneanilines with superoxide ion in acetonitrile under mild conditions to yield cyanomethyl adducts is disclosed in *Bull. Chem. Soc. Jpn,* 1986, 59, 3323. The inherent disadvantages are number of byproducts obtained along with the required amino nitrile, lengthy procedure, non-selectivity and non-catalytic nature of the reaction. *Tetrahedron Lett.* 1990, 31, 6379, discloses the Yb(CN)$_3$ catalyzed ring opening of aziridine with trimethylsilyl cyanide resulting in the formation of β-amino nitrile. The inherent disadvantage is the critical preparation of catalyst, handling, storage and non-reusability. Preparation of chiral β-N,N-dibenzylamino nitrites in enantiomerically pure form from α-amino acids by deprotonation and stereoselective alkylation is described in *Tetrahedron Lett.* 1994, 47, 8769. The drawbacks are longer reaction times and usage of multistep procedure. The reaction of N-diphenyl phosphinyl protected aziridines with a range of nucleophiles including trimethylsilylnitrile is reported in *Synlett* 1994, 145. The drawback is the use of expensive reagents and moderate yields.

OBJECTS OF THE INVENTION

The main object of the present invention is the preparation of β-amino nitrites which are precursors for β-amino acids, in excellent yields and selectivities by the simultaneous ring opening and concomitant substitution of various aziridines with different aliphatic and aromatic nitrites.

It is another object of the invention to provide a novel and ecofriendly process for the synthesis of N-substituted β-amino nitrites in a single pot by the simultaneous ring opening and concomitant substitution of different aziridines in the presence of various organo nitrites.

It is yet another object of the invention to provide a process for the synthesis of β-amino nitrites which dispenses with the use of multistep procedure.

It is a further object of the invention to provide a process for the synthesis of β-amino nitrites using metal triflate catalyst wherein the yields are high, and the catalyst is capable of being recovered and recycled with consistent activity.

It is yet another object of the invention to provide an economical process for the synthesis of β-amino nitrites by the ring opening and concomitant substitution of aziridines by various aromatic and aliphatic nitrites.

SUMMARY OF THE INVENTION

The novelty of the present invention ties in the design and development of simultaneous ring opening and concomitant N-substitution of various N-tosyl aziridines with different aliphatic and aromatic nitrites in presence of catalytic amount of metal triflates to afford different N-substituted β-amino nitriles in excellent yields and selectivities.

Accordingly the present invention relates to a process for the preparation of a β-amino nitrile by the simultaneous ring opening and concomitant N-substitution reaction of a N-tosyl $R^1,R^2$-aziridine wherein $R^1$ is selected from the group consisting of alkyl, aryl and cycloalkyl, $R^2$ is selected from the group consisting of H, methyl, ethyl and phenyl, with an aliphatic or aromatic nitrile of the formula $R^3$CN wherein $R^3$ is selected from the group consisting of methyl, ethyl, propyl, butyl, phenyl and benzyl, in the presence of a catalytic amount of metal triflate of the formula $M(OTf)_x$ wherein M is a metal, with continuous stirring using a solvent selected from group consisting of the aliphatic or aromatic nitrile as self-solvent, THF, DCM, benzene and toluene under nitrogen atmosphere to obtain N-substituted β-amino nitrile.

In one embodiment of the invention, $R^1$ is selected from the group consisting of phenyl, 4-methyl phenyl, 4-ethyl phenyl, 4-methoxyphenyl n-butyl, n-pentyl, n-hexyl, n-heptyl, n-octyl, cyclohexyl, cyclooctyl and benzyl.

In another embodiment of he invention, the aliphatic or aromatic nitrile reactant is selected from the group consisting of benzonitrile, propionitrile and acetonitrile.

In another embodiment of the invention, the aziridine is selected from the group consisting of N-tosylated phenyl aziridine, N-tosylated 4-(methylphenyl) aziridine, N-tosylated 2,3-diphenyl aziridine, N-tosylated n-octyl aziridine and N-tosylated cyclohexyl aziridine.

In an embodiment of the present invention, the quantity of metal triflate catalyst used in the reaction is 5–15 mol % with respect to the substrate aziridine.

In an embodiment of the present invention, the metal triflate catalyst is recovered by simple filtration and recycled for several cycles with consistent activity.

In yet another embodiment of the present invention, M is selected from the group consisting of Cu, Zn, Ru, Sc, In, La, Ce, Nd, Bi, Dy, Gd, Pr, Yb, Nd, Sm and Y.

In another embodiment of the invention, the catalyst used is scandium triflate.

In still another embodiment of the present invention, the reaction is carried out at a temperature in the range of 0 to 35° C. for a time period in the range of 1 to 23 h.

In yet another embodiment of the present invention, the reagent nitrile is also used as solvent to dispense the use of another solvent thus simplifying the work up procedure for the recovery of catalyst and products.

DETAILED DESCRIPTION OF THE INVENTION

The present invention comprises the preparation of β-amino nitrites which are precursors for β-amino acids, by the simultaneous ring opening and concomitant substitution of various N-tosyl $R^1,R^2$-aziridines with different aliphatic and aromatic nitrites $R^3CN$ in presence of catalytic amount of metal triflates $[M(OTf)_x]$ to afford different N-substituted β-tert-amino nitrites in excellent yields and selectivities, wherein the $R^1$ is selected from alkyl, aryl, cycloalkyl groups consisting of phenyl, 4-methyl phenyl, 4-ethyl phenyl, 4-methoxyphenyl, n-butyl, n-pentyl, n-hexyl, n-heptyl, n-octyl, cyclohexyl, cyclooctyl, benzyl, etc., $R^2$ is H, methyl, ethyl, phenyl, etc., $R^3$ is selected from methyl, ethyl, propyl, butyl, phenyl, benzyl, etc., and M is selected from Cu, Zn, Ru, Sc, In, La, Ce, Nd, Bi, Dy, Gd, Pr, Yb, Nd, Sm, Y, etc. The reaction is carried out in the presence of catalytic amount of metal triflates at a temperature ranging from 0 to 35° C. for 1 to 23 h with continuous stirring using solvents such as nitrite as self-solvent, THF, DCM, benzene, and toluene under nitrogen atmosphere. The process of the invention overcomes the disadvantages of the prior art enumerated above since, inter alia, the work up is simple, and the catalyst is recoverable and recyclable with consistent activity for several cycles. The synthesis of N-substituted β-amino nitrites is under mild conditions and the products can be used further to prepare N-substituted β-amino acids, β-lactams, β-peptides, etc. The use of ambient temperature and different substituted aziridines as well as nitrites provides the N-substituted β-amino nitriles as product in good to excellent yields and in a single step.

Generally the quantity of metal triflates used in the reaction is 5–15 mol % with respect to the aziridine. The metal triflate catalyst used in the reactions can be recovered by simple filtration and reuse for number of cycles with consistent activity.

The reaction is preferably carried out in the presence of catalytic amount of metal triflates at a temperature ranging from 0 to 35° C. for 1 to 23 h with continuous stirring using the nitrile as self-solvent under nitrogen atmosphere. The process comprises the unique activation of organo nitrite to facilitate simultaneous ring opening and N-substitution of activated aziridines by metal triflates to obtain N-substituted β-amino nitrites in excellent yields in a single pot. Post alkylation of β-amino acid/peptide, a tedious endeavor, is dispensed in the present protocol.

Higher yields are obtained when scandium triflate is used as catalyst. Incidentally this forms the first report of formation of N-substituted β-amino nitriles in a single pot. The consistent activity obtained for several cycles makes the process economical and possible for commercial realization.

N-substituted β-amino nitriles are widely used as intermediates for the synthesis of biologically active compounds such as N-substituted β-Amino acids, β-lactams and β-peptides, N-substitution of β-peptides exhibits increased potency and selectivity because of enhanced hydrophobicity, improved bioavailability and metabolic stability.

Scientific Explanation

The process of the invention comprises the unprecedented activation of alkyl/aryl nitrite to facilitate simultaneous ring opening and N-alkylation of activated aziridines by scandium (III)trifluoromethanesulfonate $[Sc(OTf)_3]$ to obtain N-substituted β-amino nitrites in excellent yields in a single pot arid dispenses with post alkylation of β-amino acids. In the presence of organo nitriles, the metal catalyst complexes with the nitrogen of nitrile in preference to aziridine to font a Lewis adduct. This Lewis adduct on further interaction with aziridine afforded N-substituted β-amino nitriles via an intermediate transition state. The direct activation of organo nitriles by scandium triflate opens up enormous opportunities in synthetic chemistry.

The following examples are given by way of illustration of the present invention and therefore should not be construed to limit the scope of the invention.

EXAMPLE 1

Synthesis of N-substituted β-amino nitriles:
Synthesis of N-phenyl β-amino nitrile derivative from N-tosylated phenyl aziridine To a stirred solution of $Sc(OTf)_3$ (60 mg, 0.12 mmol) dissolved in excess of dry and freshly distilled benzonitrile (3 mL), which also acts as a solvent, aziridine (218 mg, 0.8 mmol) was added under nitrogen atmosphere. The resulting mixture was stirred at 35° C. for 12 h. On completion of the reaction, the solvent was removed by rotavapor and residue was absorbed on neutral aluminium oxide. The product was eluted using ethyl acetate:hexane (25:75) to afford pure product

EXAMPLE 2

Synthesis of N-ethyl β-amino nitrite derivative from N-tosylated phenyl aziridine To a stirred solution of $Sc(OTf)_3$ (60 mg, 0.12 mmol) dissolved in excess of dry and freshly distilled propionitrile (3 mL), which also acts as a solvent, aziridine (218 mg, 0.8 mmol) was added under nitrogen atmosphere. The resulting mixture was stirred at 35° C. for 12 h. On completion of the reaction, the solvent was removed by rotavapor and residue was absorbed on neutral aluminium oxide. The product was eluted using ethyl acetate:hexane (25:75) to afford pure product.

EXAMPLE 3

Synthesis of N-methyl C-amino nitrite derivative from N-tosylated phenyl aziridine To a stirred solution of $Sc(OTf)_3$ (60 mg, 0.12 mmol) dissolved in excess of dry and freshly distilled acetonitrile (3 mL), which also acts as a solvent) aziridine (218 mg, 0.8 mmol) was added under nitrogen atmosphere. The resulting mixture was stirred at 35° C. for 12 h. On completion of the reaction, the solvent was removed by rotavapor and residue was absorbed on neutral aluminium oxide. The product was eluted using ethyl acetate:hexane (25:75) to afford pure product.

EXAMPLES 4–6

The same procedure described as in examples 1–3 was followed using N-tosylated 4-(methylphenyl) aziridine to afford the corresponding products as shown in Scheme 1 and Table 1.

EXAMPLE 7
Synthesis of N-phenyl β-amino nitrile derivative from N-tosylated 2,3-diphenyl aziridine To a stirred solution of Sc(OTf)$_3$ (60 mg, 0.12 mmol) dissolved in excess of dry and freshly distilled benzonitrile (3 mL), which also acts as a solvent, aziridine (279 mg, 0.8 mmol) was added under nitrogen atmosphere. The resulting mixture was stirred at 35° C. for 23 h. On completion of the reaction, the solvent was removed by rotavapor and residue was absorbed on neutral aluminium oxide. The product was eluted using ethyl acetate:hexane (25:75) to afford pure product.

EXAMPLE 8
Synthesis of N-ethyl β-amino nitrile derivative from N-tosylated 2,3-diphenyl aziridine To a stirred solution of Sc(OTf)$_3$ (60 mg, 0.12 mmol) dissolved in excess of dry and freshly distilled propionitrile (3 mL), which also acts as a solvent, aziridine (279 mg, 0.8 mmol) was added under nitrogen atmosphere. The resulting mixture was stirred at 35° C. for 23 h. On completion of the reaction, the solvent was removed by rotavapor and residue was absorbed on neutral aluminium oxide. The product was eluted using ethyl acetate hexane (25:75) to afford pure product.

EXAMPLE 9
Synthesis of N-methyl β-amino nitrile derivative from N-tosylated 2,3-diphenyl aziridine To a stirred solution of Sc(OTf)$_3$ (60 ng, 0.12 mmol) dissolved in excess of dry and freshly distilled acetonitrile (3 mL), which also acts as a solvent, aziridine (279 mg, 0.8 mmol) was added under nitrogen atmosphere. The resulting mixture was stirred at 35° C. for 23 h. On completion of the reaction, the solvent was removed by rotavapor and residue was absorbed on neutral aluminium oxide. The product was eluted using ethyl acetate:hexane (25:75) to afford pure product.

EXAMPLES 10–12

The same procedure described as in examples 7–9 was followed using N-tosylated n-octyl aziridine to afford the corresponding products as shown in Scheme 1 and Table 1.

Scheme 1.
Ring opening of aziridines with organo nitriles.

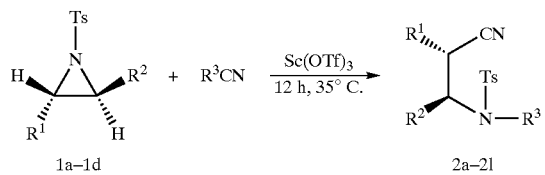

TABLE I

Sc(OTf)$_3$ Catalyzed Reaction of Aziridines with Organo Nitriles to β-tert Amino Nitriles.[a],[b]

| Example | R$^1$ | R$^2$ | R$^3$ | Time[h]/ Temp[° C.] | Product | Yield [%][c] |
|---|---|---|---|---|---|---|
| 1 | C$_6$H$_5$ | H | C$_6$H$_5$ | 12/35 | 2a | 94 |
| 2 | C$_6$H$_5$ | H | C$_2$H$_5$ | 12/35 | 2b | 92 |
| 3 | C$_6$H$_5$ | H | CH$_3$ | 12/35 | 2c | 97 |
| 4 | 4-MeC$_6$H$_4$ | H | C$_6$H$_5$ | 12/35 | 2d | 93 |
| 5 | 4-MeC$_6$H$_4$ | H | C$_2$H$_5$ | 12/35 | 2e | 95 |
| 6 | 4-MeC$_6$H$_4$ | H | CH$_3$ | 12/35 | 2f | 96 |
| 7 | C$_6$H$_5$ | C$_6$H$_5$ | C$_6$H$_5$ | 23/35 | 2g | 76 |
| 8 | C$_6$H$_5$ | C$_6$H$_5$ | C$_2$H$_5$ | 23/35 | 2h | 64 |
| 9 | C$_6$H$_5$ | C$_6$H$_5$ | CH$_3$ | 23/35 | 2i | 79 |
| 10 | CH$_3$(CH$_2$)$_7$ | H | C$_6$H$_5$ | 23/35 | 2j | 91 |
| 11 | CH$_3$(CH$_2$)$_7$ | H | C$_2$H$_5$ | 23/35 | 2k | 93 |
| 12 | CH$_3$(CH$_2$)$_7$ | H | CH$_3$ | 23/35 | 2l | 94 |

[a]reaction conditions: aziridine (0.8 mmol), Sc(OTf)$_3$ (15 mol %), nitrite (3 ml).
[b]products are characterized on the basis of spectroscopic data.
[c]isolated yield based on the aziridine used.

EXAMPLES 12–15

The same procedure described as in examples 7–9 was followed using N-tosylated cyclohexyl aziridine to afford the corresponding products as shown in Scheme 2.

Scheme 2.
Reaction of cyclohexyl aziridine with organo nitriles

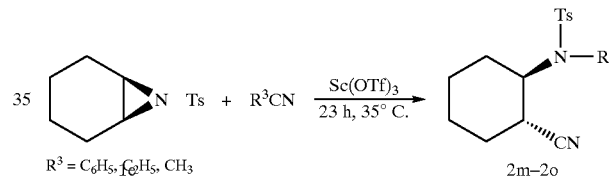

EXAMPLES 16–20

In effort to compare the reactivity of Sc(OTf)$_3$ with other triflates, cerium, bismuth, ytterbium and yttrium triflates was used. To a stirred solution of M(OTf)$_3$ (60 mg, 0.12 mmol) dissolved in excess of dry and freshly distilled acetonnitrile (3 mL), which also acts as a solvent, N-tosylated phenyl aziridine (218 mg, 0.8 mmol) was added under nitrogen atmosphere. The resulting mixture was stirred at 35° C. for 12 h. On completion of the reaction, the solvent was removed by rotavapor and residue was absorbed on neutral aluminium oxide. The product was eluted using ethyl acetate: hexane (25:75) to afford pure product. These results indicate that while the yields are good with other metal triflates, scandium triflate is the best catalyst for the formation N-substituted β-amino nitriles.

Scheme 3.
Reaction to study the catalytic Effect of various Metal Triflates

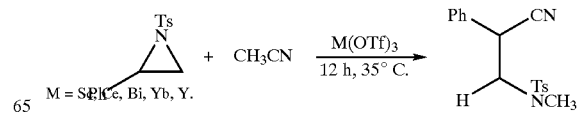

TABLE 2

Catalytic Effect of various Metal Triflates in the Reaction of Aziridine with Acetonitrile to form β-Amino Nitrile.

| Example | Metal triflate | Time(h)/temp(° C.) | Product Yield % |
|---|---|---|---|
| 16 | Scandium triflate | 12/35 | 97 |
| 17 | Cerium triflate | 12/35 | 82 |
| 18 | Bismuth triflate | 12/35 | 71 |
| 19 | Ytterbium triflate | 12/35 | 66 |
| 20 | Yttrium triflate | 12/35 | 63 |

EXAMPLES 21–24

In an effort to compare the formation of N-methyl β-amino nitrile derivative with different solvents a variety of solvents, such as benzene, dichloromethane, toluene and THF were used for the reaction of acetonitrile with N-tosylated phenylaziridine under identical reaction conditions. The yield of amino nitrile was found to reduce significantly (Table 3). When THF was used as a solvent, polymerization took place and a gel like mass was obtained. To a stirred solution of Sc(OTf)$_3$ (60 mg, 0.12 mmol) dissolved in dry and freshly distilled solvent, acetonitrile (36 mg, 0.88 mmol) and N-tosylated phenyl aziridine (218 mg, 0.8 mmol) was added under nitrogen atmosphere. The resulting mixture was stirred at 35° C. for 12 h. On completion of the reaction, the solvent was removed by rotavapor and residue was absorbed on neutral aluminium oxide. The product was eluted using ethyl acetate:hexane (25:75) to afford pure product. These results indicate that nitrites act as the best solvent for the formation N-substituted β-amino nitriles.

TABLE 3

Effect of solvents on scandium triflate catalyzed ring opening reaction of N-tosylated phenyl aziridine with acetonitrile

| Example | Solvents | Time(h) | Temp.(° C.) | Yield % |
|---|---|---|---|---|
| 21 | Benzene | 12 | 35 | 40 |
| 22 | Toluene | 12 | 35 | 69 |
| 23 | Dichloromethane | 12 | 35 | 58 |
| 24 | THF | 12 | 35 | — |

The Main Advantages of the Present Invention are:
1. A novel and ecofriendly process for the synthesis of N-substituted β-amino nitrites in a single pot by the simultaneous ring opening and concomitant substitution of different aziridines in the presence of various organo nitriles is presented.
2. The present process dispenses the use of multistep procedure instead a single pot reaction is carried out.
3. Scandium triflate is found to be the best catalyst in terms of yield, ease of handling and storage.
4. The yields are excellent in most of the examples.
5. The work-up procedure is simple.
6. The catalyst is subjected to many recycles, which displayed consistent activity.
7. The present process is environmentally safe since there is no disposal problem.
8. The process is economical.

We claim:

1. A process for the preparation of a β-amino nitrile by the simultaneous ring opening and concomitant N-substitution reaction of a N-tosyl $R^1,R^2$-aziridine wherein $R^1$ is selected from the group consisting of alkyl aryl and cycloalkyl, $R^2$ is selected from the group consisting of H, methyl, ethyl and phenyl, with an aliphatic or aromatic nitrile of the formula $R^3CN$ wherein $R^3$ is selected from the group consisting of methyl, ethyl, propyl, butyl, phenyl and benzyl, in the presence of a catalytic amount of metal triflate of the formula $M(OTf)_x$ wherein M is a metal, with continuous stirring using a solvent selected from group consisting of the aliphatic or aromatic nitrile as self-solvent, THF, DCM, benzene and toluene under nitrogen atmosphere to obtain N-substituted β-amino nitrile.

2. A process as claimed in claim 1 wherein $R^1$ is selected from the group consisting of phenyl, 4-methyl phenyl, 4-ethyl phenyl, 4-methoxyphenyl, n-butyl, n-pentyl, n-hexyl, n-heptyl, n-octyl, cyclohexyl, cyclooctyl and benzyl.

3. A process as claimed in claim 1 wherein the aliphatic or aromatic nitrile reactant is selected from the group consisting of benzonitrile, propionitrile and acetonitrile.

4. A process as claimed in claim 1 wherein the aziridine is selected from the group consisting of N-tosylated phenyl aziridine, N-tosylated 4-(methylphenyl) aziridine, N-tosylated 2,3-diphenyl aziridine, N-tosylated n-octyl aziridine and N-tosylated cyclohexyl aziridine.

5. A process as claimed in claim 1 wherein the quantity of metal triflate catalyst used is 5–15 mol % with respect to the substrate aziridine.

6. A process as claimed in claim 1 wherein the metal triflate catalyst is recovered by filtration and recycled to the reactor for several cycles with consistent activity.

7. A process as claimed in claim 1 wherein M is selected from the group consisting of Cu, Zn, Ru, Sc, In, La, Ce, Nd, Bi, Dy, Gd, Pr, Yb, Nd, Sm and Y.

8. A process as claimed in claim 1 wherein the catalyst used is scandium triflate.

9. A process as claimed in claim 1 wherein the reaction is carried out at a temperature in the range of 0 to 35° C. for a time period in the range of 1 to 23 h.

* * * * *